(12) United States Patent
Sarangapani et al.

(10) Patent No.: US 11,944,379 B2
(45) Date of Patent: Apr. 2, 2024

(54) SYSTEMS AND METHODS FOR USING MACHINE LEARNING TO PREDICT CONTACT LENS COMPATIBILITY

(71) Applicant: Alcon Inc., Fribourg (CH)

(72) Inventors: Ramesh Sarangapani, Coppell, TX (US); Kevin Baker, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 884 days.

(21) Appl. No.: 16/896,006

(22) Filed: Jun. 8, 2020

(65) Prior Publication Data

US 2020/0405145 A1     Dec. 31, 2020

Related U.S. Application Data

(60) Provisional application No. 62/867,362, filed on Jun. 27, 2019.

(51) Int. Cl.
| | |
|---|---|
| *A61B 3/00* | (2006.01) |
| *G06N 5/04* | (2023.01) |
| *G06N 20/00* | (2019.01) |
| *G16H 50/20* | (2018.01) |
| *G16H 50/70* | (2018.01) |

(52) U.S. Cl.
CPC ............. *A61B 3/0025* (2013.01); *G06N 5/04* (2013.01); *G06N 20/00* (2019.01); *G16H 50/20* (2018.01); *G16H 50/70* (2018.01)

(58) Field of Classification Search
CPC .......... A61B 3/0025; A61B 3/04; G06N 5/04; G06N 20/00; G16H 50/20; G16H 50/70; G02C 7/047; G02C 13/003; G02C 7/04

USPC ......................................................... 351/206
See application file for complete search history.

(56) References Cited

U.S. PATENT DOCUMENTS

| | | | |
|---|---|---|---|
| 2009/0195749 A1* | 8/2009 | Blum ................... | G02C 7/101 351/159.44 |
| 2014/0300860 A1 | 10/2014 | Tanaka et al. | |
| 2016/0156424 A1* | 6/2016 | Mirbagheri ............ | H04J 11/004 375/227 |
| 2016/0321691 A1* | 11/2016 | Bott ................... | G06Q 30/0255 |
| 2017/0371178 A1* | 12/2017 | Crespo ................. | G02C 7/027 |
| 2018/0098342 A1* | 4/2018 | Jiang ................. | H04W 56/0035 |

FOREIGN PATENT DOCUMENTS

| | | |
|---|---|---|
| EP | 1496345 A1 | 1/2005 |
| WO | 2005079546 A3 | 4/2007 |

* cited by examiner

*Primary Examiner* — Mohammed A Hasan

(57) ABSTRACT

Systems and methods for determining a compatibility between a multi-focal contact lens and a patient seeking presbyopia vision correction include receiving, from a first device associated with a first eye-care professional (ECP), a request for selecting a contact lens for a consumer, wherein the request comprises biometric information associated with the consumer; obtaining a performance metric associated with the first ECP; determining, using the machine learning model and based on the performance metric, a customized compatibility index indicating a compatibility between a particular contact lens and the consumer for the first ECP; and presenting a report indicating the compatibility index on the first device. Additional systems, methods, and non-transitory machine-readable mediums are also provided.

13 Claims, 11 Drawing Sheets

SYSTEMS AND METHODS FOR USING MACHINE LEARNING TO PREDICT CONTACT LENS COMPATIBILITY

BACKGROUND

Field of the Disclosure

The present disclosure relates to using machine learning to predict lens compatibility for different users according to various embodiments of the disclosure.

Description of Related Art

The technologies in manufacturing contact lenses have seen substantial improvement over the recent years such that most contact lenses can fit comfortably for most users. However, certain types of contact lenses, such as multi-focal contact lenses, remains difficult to fit for users. Conventionally, fitting contact lenses (e.g., multi-focal contact lenses) for users is an enduring process. Eye-care professionals (ECPs) may recommend a type of contact lens (e.g., a particular prescription, a particular power, a particular shape such as curvature, a particular manufacturer, etc.) to a user for trial (e.g., using the recommended type of contact lens for a period of time such as two weeks). The user may have a follow-up visit after the trial to determine whether the type of contact lens is a good fit for the user or not and/or a follow-up lens fitting to determine which contact lens fits better. Due to the difficulty in fitting and the inability for the ECPs to accurately predict the outcome of the users seeking vision correction (e.g., presbyopia vision correction) using contact lenses (e.g., multi-focal contact lenses), the user may need to visit the ECP multiple times before determining a type of contact lenses that fits well for the user (or determining that the user is not a good candidate for any types of contact lenses). As a result, the cost of prescribing contact lenses to users become unnecessarily high, and in certain cases, ECPs became reluctant in recommending and/or prescribing certain types of contact lenses to users who may have been benefitted by such innovative vision correction solution. Therefore, there is a need in the art for techniques for better predicting the outcome for multi-focal contact lens users.

SUMMARY

According to some embodiments, a system includes one or more hardware processors. The one or more hardware processors are configured to receiving, from a first device associated with a first eye-care professional (ECP), a request for selecting a contact lens for a consumer, wherein the request comprises biometric information associated with the consumer; obtaining a performance metric associated with the first ECP; determining, using the machine learning model and based on the performance metric, a customized compatibility index indicating a compatibility between a particular contact lens and the consumer for the first ECP; and presenting a report indicating the compatibility index on the first device.

According to some embodiments, a method includes receiving, by one or more hardware processors from a first device associated with a first eye-care professional (ECP), a request for determining a compatibility between a particular lens and a patient, wherein the request comprises attributes associated with the patient; comparing, by the one or more hardware processors, performance information associated with the first ECP against performance information associated with at least a second ECP; determining, by the one or more hardware processors, a performance metric associated with the first ECP based on the comparing; selecting, by the one or more hardware processors from a plurality of compatibility indexes and based on the attributes associated with the patient, a particular compatibility index representing a degree of compatibility between the particular lens and the patient, wherein the compatibility index is customized for the first ECP based at least in part on the performance metric associated with the first ECP; and presenting, by the one or more hardware processors, a report indicating the particular compatibility index on the first device.

According to some embodiments, a non-transitory machine-readable medium comprising a plurality of machine-readable instructions executable to cause a machine to perform operations including receiving, from a first device associated with a first eye-care professional (ECP), a request for selecting a contact lens for a consumer, wherein the request comprises biometric information associated with the consumer; obtaining a performance metric associated with the first ECP; determining, using the machine learning model and based on the performance metric, a customized compatibility index indicating a compatibility between a particular contact lens and the consumer for the first ECP; and presenting a report indicating the compatibility index on the first device.

BRIEF DESCRIPTION OF THE DRAWINGS

For a more complete understanding of the present technology, its features, and its advantages, reference is made to the following description, taken in conjunction with the accompanying drawings.

Figure 1:
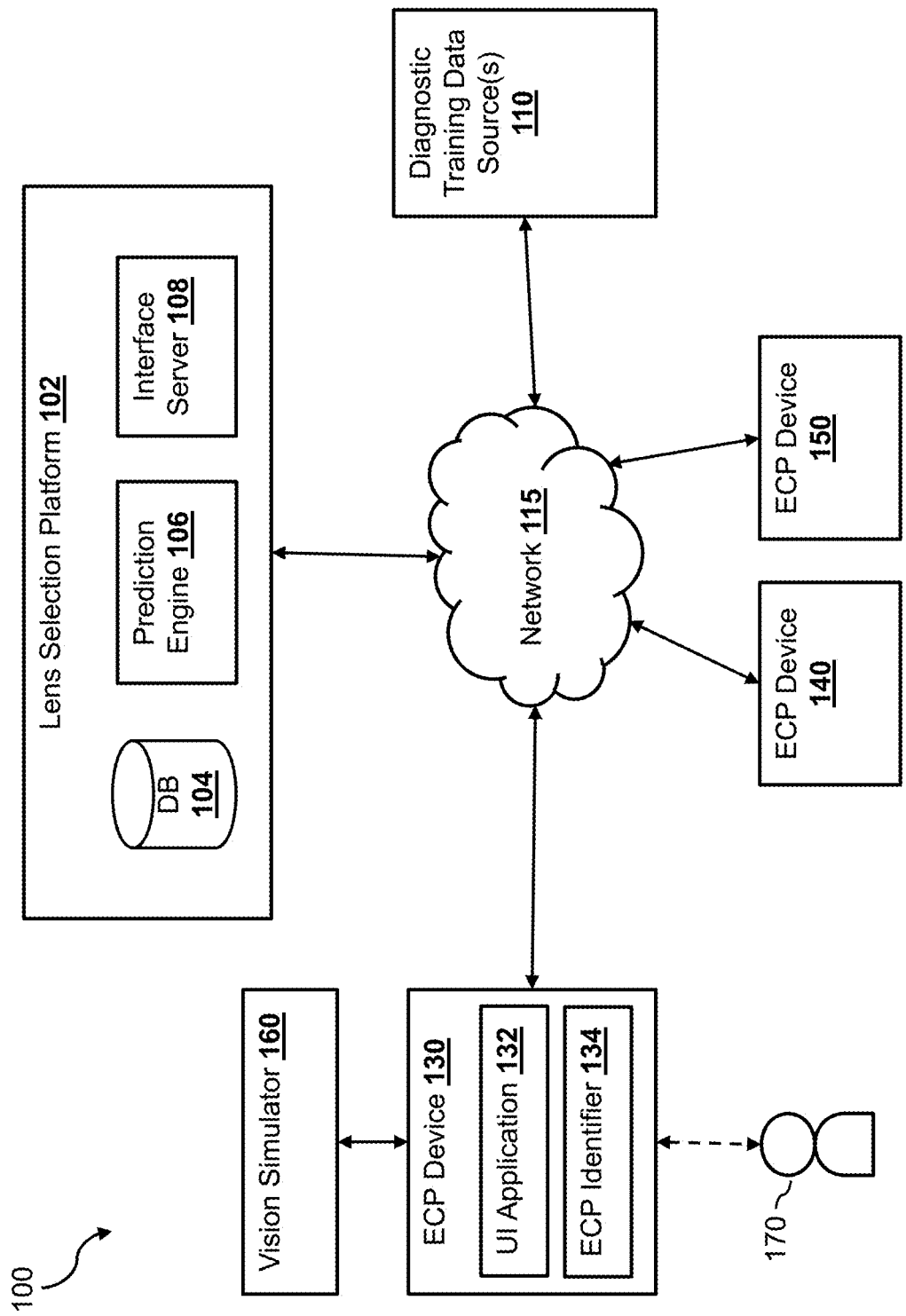
FIG. 1 is a diagram of a system for lens compatibility determination according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

The technology described below involves systems and methods to use machine learning in predicting compatibility of one or more types of lens (e.g., one or more types of contact lens) for users. As discussed above, a particular type of lens (e.g., for a particular prescription, having a particular lens power, associated with a particular manufacturer, having a particular geometric shape such as curvature, etc.) may fit differently for different users, and it is a challenge for eye-care professionals (ECPs) to determine whether the particular type of lens would fit well with a patient or not. The type of lens may be a contact lens (e.g., a multi-focal contact lens, etc.) or any type of lens for use by patients. As such, in some embodiments, a lens compatibility system may be provided to assist ECPs in recommending and/or prescribing different types of lenses to patients. In some embodiments, the lens compatibility system may provide a user interface (e.g., a graphical user interface (GUI), etc.) on devices of ECPs. The user interface may be configured to receive a compatibility request from one or more ECPs for determining whether a type of lens is compatible with a patient. The compatibility request may include attributes of a patient such as an age, an eye dryness index, a length and frequency of computer usage, a user preference (e.g., how comfortable the patient is with regular eye glasses, etc.), a motivation of the user for using the type of lens, an arm length of the user (which indicates a reading distance of the user), whether the patient has red eye issues, current prescription data, eye measurements such as a pupil diameter, etc. The lens compatibility system may use the attributes of the patient to determine whether the type of lens is compatible with the patient.

In some embodiments, the lens compatibility system may use a machine learning model to determine the compatibility between the type of lens and the patient. For example, the machine learning model may be configured to provide an output that indicates a likelihood that a patient is a good candidate for the type of lens (e.g., a compatibility score) based on attributes of the patient and other data received via the user interface. The machine learning model may be trained using historical data of patients who have been previously prescribed with the type of lens associated with the request. For example, the lens compatibility system may retrieve patient records of patients who have been prescribed the type of lens from various ECPs, including the attributes of the patients and the outcome for the users (e.g., via surveys provided to the patients after a predetermined trial period with the lens, etc.) from devices of the various ECPs. The retrieved patient records may then be used as training data for the machine learning model. The machine learning model can be implemented using one or more techniques such as a neural network, a regression model, or any other types of machine learning algorithms.

After receiving the attributes of the patient and other data via the user interface, the lens compatibility system may provide the attributes of the patient and the other data to the machine learning model as input values. Based on the attributes of the patient, the machine learning model may generate an output that indicates a likelihood that the patient is a good candidate for the type of lens. In some embodiments, the machine model may generate a compatibility score as the output. The compatibility score may represent how compatible the type of lens is for the patient based on the attributes of the patient on a scale, where one end of the scale represents very compatible and the other end of the scale represents very incompatible.

Different embodiments of the lens compatibility system may configure the machine learning model differently to generate the compatibility score to represent different facets of compatibility for the patients. For example, in some embodiments, the compatibility score may represent a predicted comfort level of the patient when wearing the lens. In another embodiment, the compatibility score may represent a predicted vision quality of the patient. In yet another embodiment, the compatibility score may represent a predicted number of lenses to be fitted for the patient and/or a predicted number of follow-up visits required by the patient. In yet another embodiment, the compatibility score may represent any combinations of the factors described above.

In some embodiments, the lens compatibility system may provide a compatibility report on the interface of the ECP device based on the output generated by the machine learning model. For example, the compatibility report may indicate a compatibility score generated by the machine learning model that indicates a likelihood that the patient is a good candidate for the type of lens. Since the machine learning model was trained using patient data of multiple ECPs (that may or may not include the ECP who submitted the request), the ECP who submitted the request may now obtain compatibility information for her patient based not only on how the type of lens fits patients of that ECP in the past, but also how the type of lens would fit patients of other ECPs. The ability of the lens compatibility system to access a large sample size of patients from different ECPs means that the accuracy of patient compatibility is improved. Furthermore, since the ECP (who submitted the request) is only provided with the compatibility report generated by the lens compatibility system, and not any patient records used to train the machine learning model, patient privacy may be preserved.

In some embodiments, the compatibility report may include the compatibility score generated by the machine learning model. However, it may be difficult for an ECP to translate the compatibility score to an actual recommendation for prescribing the type of lens to a patient. Thus, to assist the ECP in her recommendation and/or prescription, the lens compatibility system of some embodiments may derive additional data (e.g., meaning) to the compatibility score. For example, the lens compatibility system may determine multiple compatibility indices that represent different recommendations for prescribing the type of lens to the patient. In a specific, but non-limiting example, the lens compatibility system may determine three different compatibility indices, representing highly recommended, recommended, and not recommended, respectively. The compatibility indices may be associated with different, non-overlapping ranges of compatibility score. For example, if the compatibility score is generated on a scale of 1-100 by the machine learning model, a first range of 71-100 may correspond to a first compatibility index representing highly recommended, a second range of 41-70 may correspond to a second compatibility index representing recommended, and a third range of 1-40 may correspond to a third compatibility index representing not recommended. In some embodiments, the ranges may be determined based on specific outcomes of prescribing the type of lens to previous patients. In one example, the lens compatibility system may determine the first range to include compatibility scores between 71-100 based on a predetermined percentage (e.g., 90%) of the patients prescribed with the type of lens having compatibility scores within this range never needed a follow up visit with their ECPs. The lens compatibility system may determine the second range to include compatibility scores between 41-70 based on a predetermined percentage (e.g., 90%) of the patients prescribed with the type of lens having compatibility scores within this range needed only one follow up visit with their ECPs. The lens compatibility system may then determine a compatibility index for the patient based on which of the ranges does the compatibility score fall into.

Thus, in some embodiments, the lens compatibility system may present, instead of or in addition to the compatibility score, the compatibility index on the interface to assist the ECP in recommending and/or prescribing the type of lens to the patient. In some embodiments, the lens compatibility system may use the same compatibility score ranges for the compatibility indices for every ECPs. However, different ECPs may have different preferences in how they recommend or prescribe lenses to their patients. In certain scenarios, the differences in preferences may attribute to the demographics of the patients that the ECPs serve, the geographical area where the ECP is located, or ECPs' own personal preferences (e.g., how aggressive/conservative they are in prescribing the type of lens to patients). Since the machine learning model was trained with historical data of patients of different ECPs, and the model does not differentiate one ECP from another, the output (e.g., the compatibility score) of the machine learning model may be generic to all patients, and not specific to patients of one ECP. As such, in some embodiments, the lens compatibility system may determine different ranges corresponding to the different compatibility indices for different ECPs. For example, the lens compatibility system may determine, for a first ECP, that the first compatibility index (e.g., highly recommended) corresponds to a range of 81-100, the second compatibility index (e.g., recommended) corresponds to a range of 51-80, and the third compatibility index (e.g., recommended) corresponds to a range of 1-50. The lens compatibility system may determine, for a second ECP, that the first compatibility index (e.g., highly recommended) corresponds to a range of 61-100, the second compatibility index (e.g., recommended) corresponds to a range of 31-60, and the third compatibility index (e.g., recommended) corresponds to a range of 1-30.

The different ranges may be determined for the different ECPs based on various factors, such as the geographical area of the ECPs, the demographics of the patients of the ECPs, or a recommendation/prescription performance of the ECP relative to the performance of other ECPs (e.g., the ECP's peers). As such, in some embodiments, the lens compatibility system may determine a position of the ECP who submitted the request in comparison with the positions of other ECPs based on the recommendation/prescription performances of the ECPs. For example, the lens compatibility system may determine, for each ECP, a ratio of recommending/prescribing the type of lens to patients (e.g., a ratio of prescribing multi-focal lens to patients seeking presbyopia vision correction). The lens compatibility system may compare the ratio of the ECP who submitted the request against the ratios of other ECPs, and may adjust the ranges associated with the compatibility indices based on the comparison. In a specific, and non-limiting, example, if the lens compatibility system determines that the ECP who submitted the request has a lower than average ratio compared to the other ECP, the lens compatibility system may enlarge the range(s) corresponding to the first (and/or second) compatibility indices (representing highly recommended and recommended, respectively), and vice versa.

In another example, the lens compatibility system may determine, for each ECP, a number of lenses fitted for the patient and/or a number of follow-up visits (e.g., an average number) of their patients (e.g., who were prescribed with the type of lens, who were prescribed with lens from that ECP in general, etc.). The lens compatibility system may compare the number of lenses fitted for patients and/or the number of follow-up visits associated with the ECP who submitted the request against the number of lenses fitted for patients and/or the number of follow-up visits associated with other ECPs, and may adjust the ranges associated with the compatibility indices based on the comparison. In a specific, and non-limiting, example, if the lens compatibility system determines that the ECP who submitted the request has a lower than average number of lenses fitted for the patient and/or a lower than average number of follow-up visits compared to the other ECP, the lens compatibility system may enlarge the range(s) corresponding to the first (and/or second) compatibility indices (representing highly recommended and recommended, respectively), and vice versa.

In some embodiments, the lens compatibility system may include or communicatively coupled with one or more vision simulators associated with different ECP offices. The vision simulator may provide a simulation of wearing and/or using the type of lens for the patient. For example, the vision simulator may include a wearable device (e.g., a headgear, a pair of goggles, etc.) that provides the patient with a simulated vision that the patient may have when using the type of lens under one or more environments (e.g., daytime driving, nighttime driving, reading, using an electronic device such as a computer, a mobile device, etc.). In some embodiments, the vision simulator may be configured to obtain feedback from the patient (e.g., vision quality, comfort level, etc.) based on the simulation. For example, the vision simulator may be configured to prompt the patient for feedback during various portions of the simulation (e.g., during different environment simulation), such that the patient may be able to provide feedback for different simulated environment. In some embodiments, the lens compatibility system may configure the machine learning model to receive the feedback from the patient, in addition to the other attributes, as inputs and to determine the output (e.g., the compatibility score) for the patient based on the patient feedback to the vision simulation as well as the attributes. In some embodiments, the vision simulator may also include one or more sensors (e.g., a camera, a heart rate monitor, a humidity sensor, etc.) to detect and/or track biometric data associated with the patient (e.g., eye movement, eye blinking frequency, eye redness, facial expressions such as frowning, squinting, etc., heart rate, tearing, etc.) during the simulation, and may be configured to provide the detected biometric data to the lens compatibility system. Thus, the lens compatibility system may also configure the machine learning model to also receive the biometric data obtained from the vision simulator as input values and to determine an output based on the biometric data as well as other attributes of the patient.

Thus, the lens selection system according to various embodiments of the disclosure is capable of providing a customizable interface to an ECP to assist the ECP in recommending and/or prescribing a type of lens to patients by using experiences of patients associated with different ECPs without divulging sensitive and/or private data of the patients.

FIG. 1 illustrates a system 100 for lens compatibility determination within which the lens compatibility system may be implemented according to some embodiments. System 100 includes a lens selection platform 102 coupled with one or more diagnostic training data sources 110 via a network 115. In some examples, network 115 may include one or more switching devices, routers, local area networks (e.g., an Ethernet), wide area networks (e.g., the Internet), and/or the like. Each of the diagnostic training data sources 110 may be a database, a data repository, and/or the like made available by an, ECP practice, an eye clinic, a medical university, an electronic medical records (EMR) repository, and/or the like. Each of the diagnostic training data sources 110 may provide the lens selection platform 105 with training data in the form of patient records of patients who have been prescribed with one or more types of lens (e.g., multi-focal lens, etc.). Each patient record may include attributes of a corresponding patient seeking vision correction associated with the type of lens (e.g., a patient seeking presbyopia vision correction, etc.), such as an age, an eye dryness index, a length and frequency of computer usage, a user preference (e.g., how comfortable the patient is with regular eye glasses, etc.), a motivation of the user for using the type of lens, an arm length of the user (which indicates the reading distance of the user), whether the patient has red eye issues, current prescription data, eye measurements such as a pupil diameter, etc., and an outcome of the patient, which may indicate whether the patient was indeed prescribed with the type of lens (e.g., a multi-focal contact lens) and if the patient was indeed prescribed with the type of lens, a quality of the prescription (e.g., comfort level, vision quality level, a number of lenses fitted for the patient, a number of follow-up visits, etc.) after the patient is prescribed with the type of lens. The lens selection platform 102 may store the training data in one or more databases 104 which may be configured to anonymize, encrypt, and/or otherwise safeguard the training data.

The lens selection platform 102 includes a prediction engine 106 which may (as explained in greater detail below) process the received training data, perform raw data analysis on the training data, train machine learning algorithms and/or models to predict a compatibility between the type of lens and a patient based on the attributes of the patient, and iteratively refine the machine learning to optimize the various models used to predict the compatibility between a type of lens and patients to assist ECPs in recommending and/or prescribing the type of lens to patients.

The lens selection platform 102 is further coupled, via network 115, to one or more ECP devices, such as ECP devices 130, 140, and 150. Each of the ECP devices may be associated with an ECP. For example, the ECP device 130 is associated with an ECP 170. As shown, the ECP device 130 includes a user interface application 132, which may be a web browser, a desktop application, or a mobile application provided by the lens selection platform 102. The user interface application 132 enables the ECP device 130 to interact with the lens selection platform 102. The ECP device 130 may also include an ECP identifier 134, which may be implemented as an identifier associated with the ECP 170, a device identifier associated with the ECP device 130, or any other type of identifier to distinguish the ECP 170 from other ECPs.

In some embodiments, the ECP device 130 may be communicatively coupled with a vision simulator 160. The vision simulator 160 may include a wearable device (e.g., a headgear, a pair of goggles, etc.) and configured to provide a simulation of wearing and/or using the type of lens for patients of the ECP 170 under one or more environments (daytime driving, nighttime driving, reading, using an electronic device such as a computer, a mobile device, etc.). In some embodiments, the vision simulator 160 may also include one or more sensors (e.g., a camera, a heart rate monitor, a humidity sensor, etc.) for obtaining biometric data of the patient (e.g., eye movement, eye blinking frequency, eye redness, facial expressions such as frowning, squinting, etc., heart rate, tearing, etc.) during a simulation. Although not shown in the figure, each of the ECP devices 140 and 150 may also include similar modules and/or components as the ECP device 130. Furthermore, each of the ECP devices 140 and 150 may also be coupled to a corresponding vision simulator that is similar to the vision simulator 160.

Figure 2:
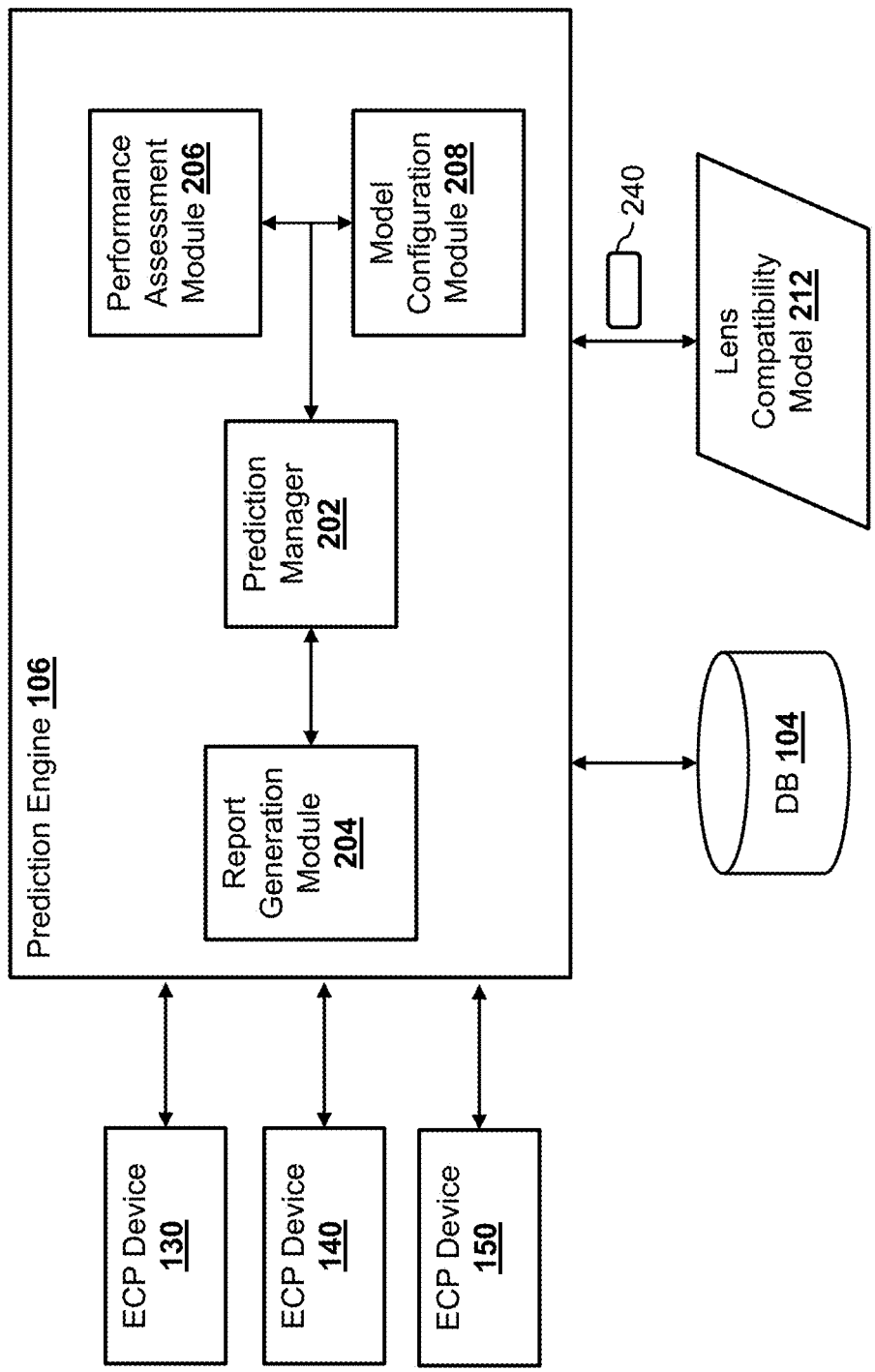
FIG. 2 is a block diagram of a prediction engine according to some embodiments.

FIG. 2 illustrates a block diagram of the prediction engine 106 according to some embodiments of the disclosure. The prediction engine 106 is communicatively coupled to various ECP devices, such as ECP devices 130, 140, and 150. The prediction engine 106 includes a prediction manager 202, a report generation module 204, a performance assessment module 206, and a model configuration module 208. The model configuration module 208 may use the training data stored in the database 104 to train a machine learning model, such as a lens compatibility model 212, to predict a compatibility of a type of lens for a patient based on information such as attributes of the patient, patient feedback from a vision simulation, and biometric information obtained during the vision simulation. The prediction manager 202 may provide a user interface (e.g., a GUI) to be presented on the ECP devices 130-150. In some embodiments, an ECP (e.g., the ECP 170) may use an ECP device (e.g., the ECP device 130) to submit a compatibility request via the user interface. For example, when the user interface application 132 receives an indication that the ECP would like to submit a compatibility request, the user interface application 132 may present an input interface associated with the prediction engine 106. The input interface may include multiple input fields that enable the ECP to provide information associated with the request (e.g., the type of lens, attributes of the patient, etc.).

In some embodiments, upon receiving the indication, the prediction manager 202 may also configure a vision simulator (e.g., the vision simulator 160) associated with the ECP device to provide a vision simulation for the patient based on the type of lens. The vision simulator 160 may obtain patient feedback and/or biometric data of the patient during the simulation and may provide the patient feedback and/or biometric data to the ECP device 130.

The user interface application 132 may then transmit data associated with the compatibility request, such as the information obtained via the input interface, the patient feedback, and the biometric data to the prediction engine 106 over the network 115. Upon receiving the compatibility request and the data (e.g., data 240), the prediction manager 202 may use the lens compatibility model 212 to determine a compatibility of the type of lens for the patient based on the data 240. The lens compatibility model 212 may generate an output (e.g., a compatibility score) based on the data 240. Using the output from the lens compatibility model 212, the report generation module 204 may generate a compatibility report to be presented on a report interface on the user interface application 132.

The ECP may recommend and/or prescribe the type of lens to the patient based on the report presented on the user interface application 132. After presenting the compatibility report on the ECP device, the prediction manager may present a feedback interface on the user interface application 132, so that the ECP may provide information related to an outcome of prescribing the type of lens to the patient. For example, the ECP may provide on the feedback interface information such as a comfort level, a vision quality level, etc. of the patient after using the type of lens for a predetermined trial period. The ECP may also provide information such as a number of lenses fitted for the patient and/or a number of follow-up visits by the patient after being prescribed with the type of lens. The prediction manager 202 may receive, via the feedback interface, the feedback information associated with prescribing the type of lens to the patient. The prediction manager 202 may use the feedback information and the attributes of the patient to update (e.g., train) the lens compatibility model 212.

The prediction manager 202 may provide compatibility reports for patients of different ECPs and receive the corresponding feedback data through different ECP devices (e.g., the ECP devices 130-150). The prediction manager 202 of some embodiments may use the performance assessment module 206 to assess the performance of each ECP. For example, the performance may be based on a ratio of prescribing the type of lens to the patients, a number of lenses fitted for the patient, and/or a number of follow-up visits after prescribing the type of lens to the patients. In some embodiments, the prediction manager 202 may present a performance assessment report to the ECPs via the user interface. Furthermore, the report generation module 204 may adjust a configuration the compatibility report (e.g., modifying the ranges of compatibility scores corresponding to the compatibility indices) for each ECP based on the performance of the ECP relative to the performances of other ECPs.

Figure 3:
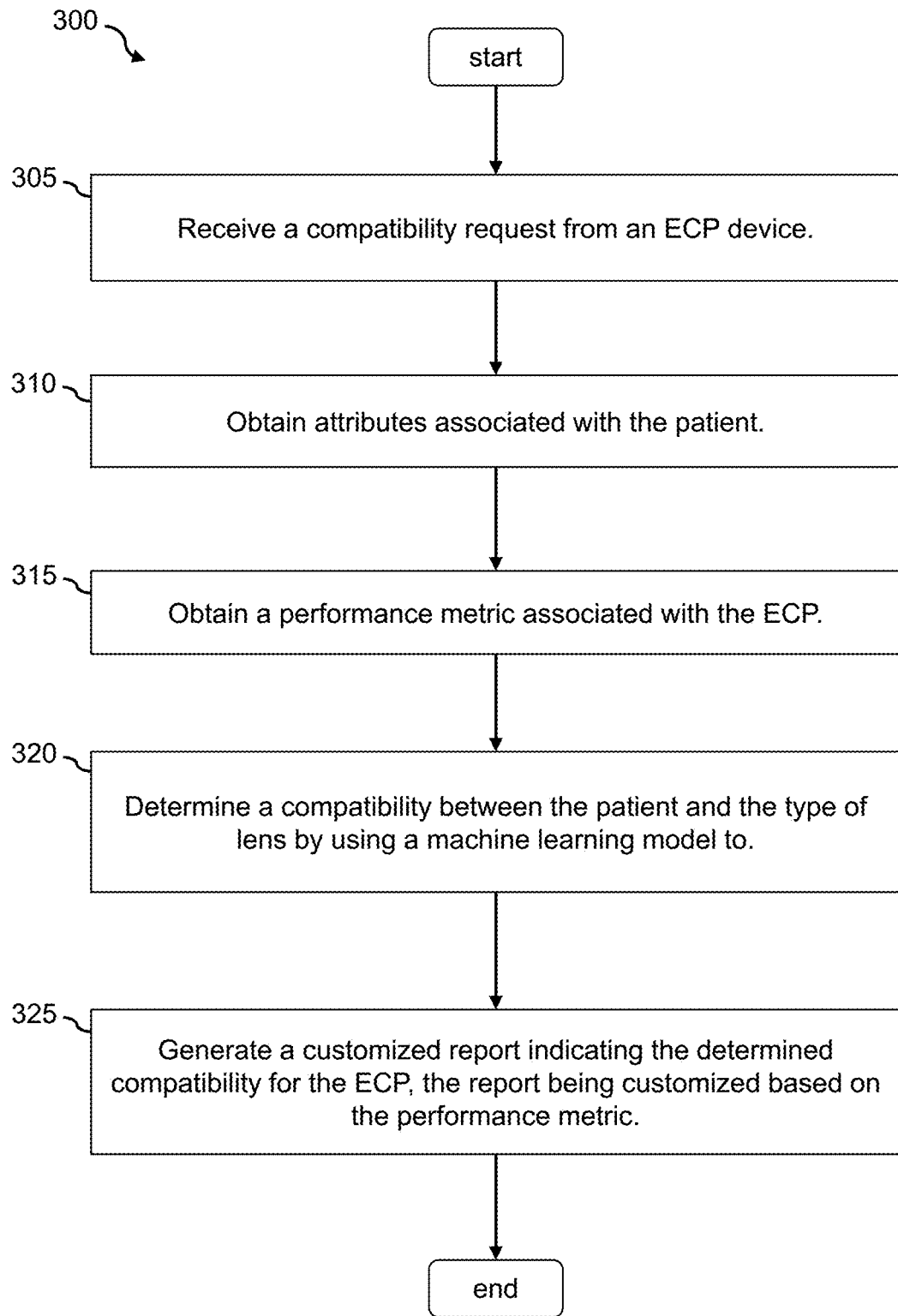
FIG. 3 illustrates a process of determining a compatibility between a lens and a patient according to some embodiments.

FIG. 3 illustrates a process 300 for determining a compatibility of a type of lens for a patient according to one embodiment of the disclosure. In some embodiments, the process 300 may be performed by the prediction engine 106 of the lens selection platform 102. The process 300 begins by receiving (at step 305) a compatibility request from an ECP device and obtaining (at step 310) attributes associated with a patient. For example, when the prediction manager 202 receives an indication, via the user interface application 132 of the ECP device 130, that the ECP 170 wants to submit a compatibility request, the prediction manager 202 may provide an input interface to be displayed on the user interface application 132. The input interface may include multiple input fields that enable the ECP 170 to provide information related to the compatibility request. The input fields may correspond to information such as a type of lens that the ECP 170 wants to determine whether to recommend and/or prescribe to a patient, attributes of the patient such as an age, an eye dryness index, a length and frequency of computer usage, a user preference (e.g., how comfortable the patient is with regular eye glasses, etc.), a motivation of the user for using the type of lens (e.g., the multi-focal contact lens, etc.), an arm length of the user (which indicates the reading distance of the user), whether the patient has red eye issues, current prescription data, eye measurements such as a pupil diameter, etc.

Figure 4A:
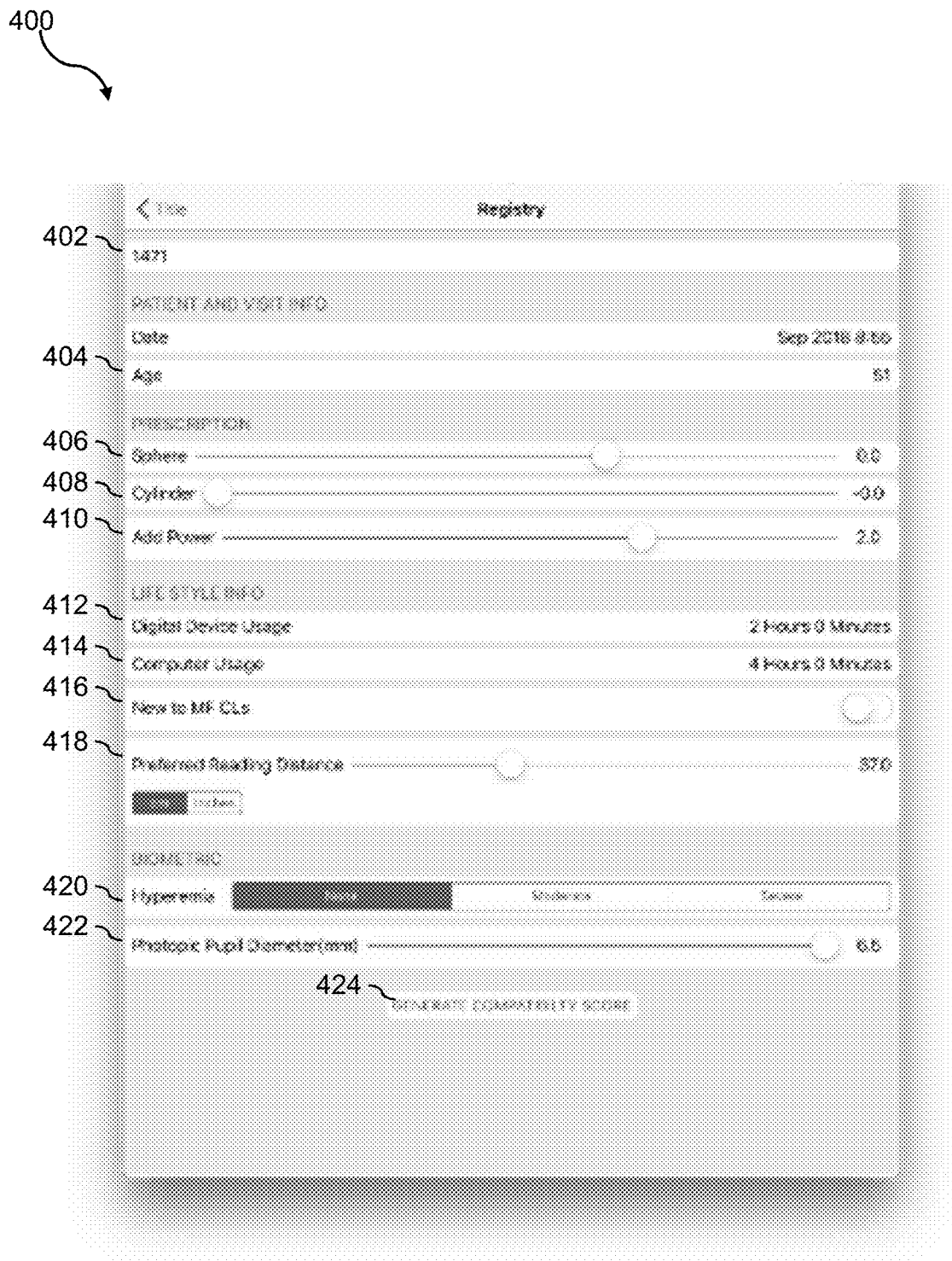
FIG. 4A illustrates an exemplary input interface according to some embodiments.

FIG. 4A illustrates an example input interface 400 according to one embodiment of the disclosure. As shown, the input interface 400 includes an input field 402 that indicates an identity of the ECP 170. The identity can be represented by an ECP identifier associated with the ECP 170, a device identifier associated with the ECP device 130, or any other type of identifiers that can distinguish the ECP 170 from other ECPs. In this example, an identifier of '1471' is displayed on the input field 402. The identifier may be automatically retrieved by the user interface from the ECP device 130 (e.g., a cookie or a registry stored on the ECP device 130, etc.). The input interface 400 also includes a field 404 representing an age of the patient. The input interface 400 also includes fields 406-410 representing current prescription data such as sphere data, cylinder data, and lens power data. The input interface 400 also includes fields 412-418 representing lifestyle data of the patient such as a daily digital device usage, a daily computer usage, whether the patient is new to the type of lens (e.g., multi-focal contact lens, etc.), and a preferred reading distance. The input interface 400 also includes fields 420 and 422 representing biometric information of the patient such as whether the patient has hyperemia and photopic pupil diameter. The ECP 170 may enter the corresponding information of the patient on the fields 402-422.

In some embodiments, since different ECPs may emphasize certain attributes of a patient and de-emphasize other attributes of patients when recommending and/or prescribing the type of lens to the patients, an ECP may select, from a set of attributes, a subset of the attributes for determining a compatibility of the type of lens for patients. The prediction engine 106 may store the preference data of each ECP in a database, such as the database 104. Thus, the prediction engine 106 may configure the input interface 400 for an ECP (e.g., based on the ECP identifier) according to the preferences of the ECP. For example, upon receiving the indication that the ECP wants to submit a compatibility request, based on an identity of the ECP (e.g., the ECP 170) the prediction engine 106 may configure the input interface 400 to present only the input fields corresponding to the subset of attributes elected by the ECP.

In some embodiments, the ECP device (e.g., the ECP device 130) may be communicatively coupled with one or more biometric instrument in the office of the ECP. As the biometric instrument is used (by the ECP 170) to determine the biometric information (e.g., a pupil diameter, etc.) of the patient, the biometric instrument may automatically provide the biometric information to the input interface 400 (e.g., pre-filling some of the input fields on the input interface 400), without requiring the ECP 170 to manually transfer the biometric information from the biometric instrument to the input interface 400. The ECP 170 may submit the compatibility request using the information provided on the input interface 400 by selecting the compatibility request button 424. Upon receiving a selection of the compatibility request button 424, the input interface 400 may automatically transmit the information obtained from the input fields to the prediction engine 106.

In some embodiments, the lens selection platform 102 and/or the ECP device (e.g., the ECP device 130) may be communicatively coupled with a vision simulator (e.g., the vision simulator 160) associated with the ECP office of the ECP 170. The vision simulator 160 may provide a simulation of wearing and/or using the type of lens for the patient. For example, the vision simulator 160 may include a wearable device (e.g., a headgear, a pair of goggles, etc.) that provides the patient with a simulated vision that the patient may have when using the type of lens under one or more environments (e.g., daytime driving, nighttime driving, reading, using an electronic device such as a computer, a mobile device, etc.). In some embodiments, the vision simulator 160 may be configured to obtain feedback from the patient (e.g., vision quality, comfort level, etc.) based on the simulation. For example, the vision simulator 160 may be configured to prompt the patient for feedback during various portions of the simulation (e.g., during different environment simulation), such that the patient may be able to provide feedback for different simulated environment. In some embodiments, the model configuration module 208 may configure the lens compatibility model 212 to receive the feedback from the patient, in addition to the other attributes, as inputs and to determine the output (e.g., the compatibility score) for the patient based on the patient feedback to the vision simulation as well as the attributes. In some embodiments, the vision simulator 160 may also include one or more sensors (e.g., a camera, a heart rate monitor, a humidity sensor, etc.) to detect and/or track biometric data associated with the patient (e.g., eye movement, eye blinking frequency, eye redness, facial expressions such as frowning, squinting, etc., heart rate, tearing, etc.) during the simulation, and may be configured to provide the detected biometric data to the prediction engine 106. Thus, the model configuration module 208 may also configure the lens compatibility model 212 to also receive the biometric data obtained from the vision simulator 160 as input values and to determine an output based on the biometric data as well as other attributes of the patient.

Figure 5:
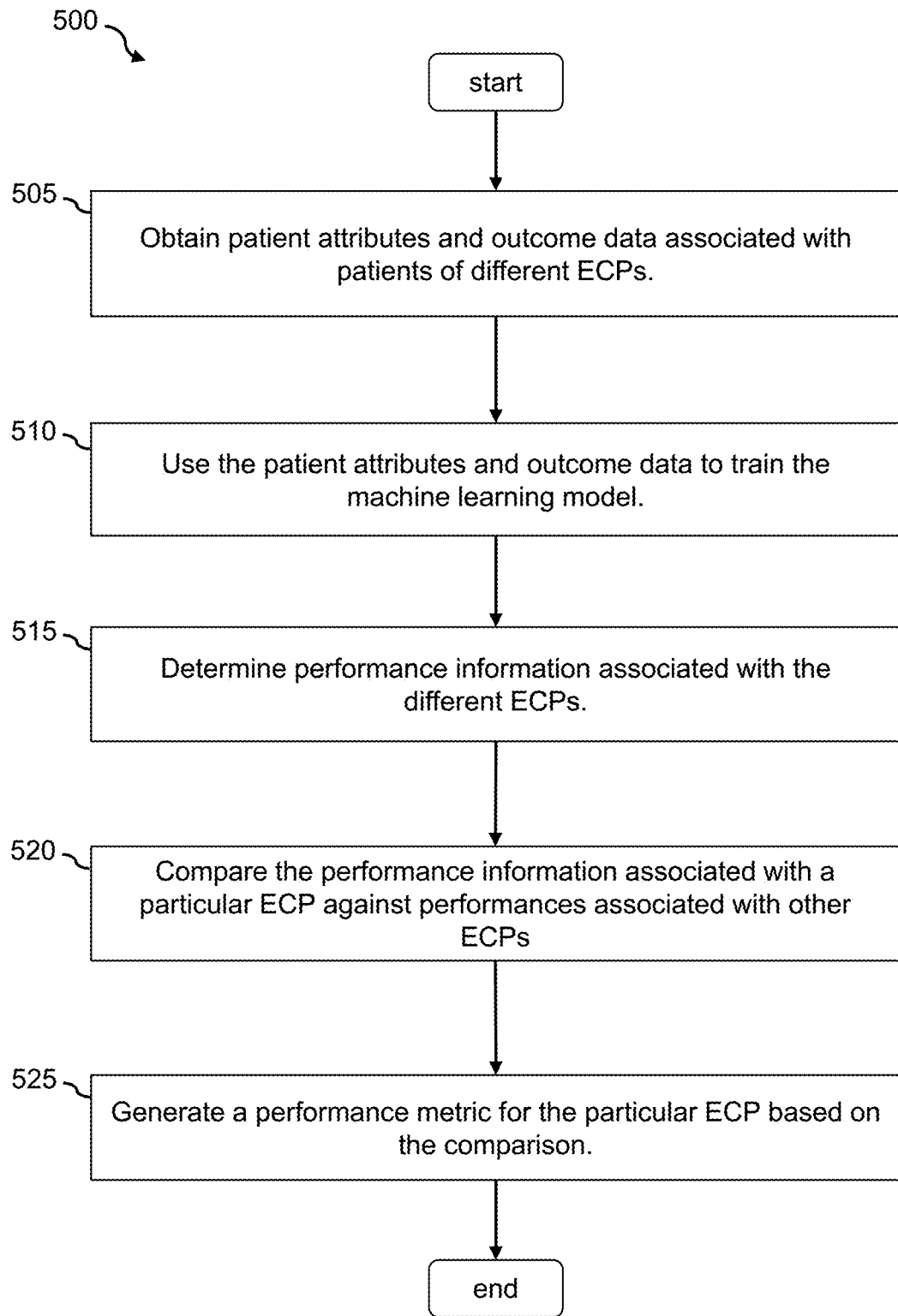
FIG. 5 illustrates a process of determining a performance metric for an eye-care professional according to some embodiments.

The process 300 then obtains (at step 320) a performance metric associated with the ECP. For example, the performance assessment module 206 may generate a performance metric associated with the ECP based on a comparison of the performance of the ECP against the performances of other ECPs. FIG. 5 illustrates a process 500 for generating a performance metric for an ECP. In some embodiments, the process 500 may be performed by the performance assessment module 206 and/or the model configuration model 208 of the prediction engine 106. The process 500 begins by obtaining (at step 505) patient attributes and outcome data associated with patients of different ECPs. For example, the performance assessment module 206 may obtain patient records that were retrieved from the diagnostic training data source(s) 110, which contain attributes and outcome of patients. In some embodiments, each patient record may include attributes of a corresponding patient seeking vision correct associated with the type of lens (e.g., a patient seeking presbyopia vision correction, etc.), such as an age, an eye dryness index, a length and frequency of computer usage, a user preference (e.g., how comfortable the patient is with regular eye glasses, etc.), an arm length of the user (which indicates the reading distance of the user), whether the patient has red eye issues, current prescription data, eye measurements such as a pupil diameter, etc., and an outcome of the patient, which may indicate whether the patient was indeed prescribed with the type of lens (e.g., a multi-focal contact lens) and if the patient was indeed prescribed with the type of lens, a quality of the prescription (e.g., comfort level, vision quality level, a number of lenses fitted for the patient, a number of follow-up visits, etc.) after the patient is prescribed with the type of lens.

In some embodiments, after the prediction engine 106 provides a recommendation (e.g., in the form of a compatibility score and/or a compatibility index, etc.) to the ECP, the prediction engine 106 may track a progress and/or an outcome of the patient. For example, the prediction engine 106 may obtain information from the ECP that indicates whether the ECP indeed prescribed the type of lens to the patient, and if the ECP did prescribe the type of lens to the patient, the prediction engine 106 may obtain outcome data such as a number of lenses fitted for the patient, a number of follow-up visits by the patient, a comfort level of the type of lens to the patient, a vision quality (e.g., overall vision quality, distance vision quality, intermediate vision quality, etc.) of the patient after using the type of lens, whether the patient is still wearing the type of lens after a predetermined period of time (e.g., 6 months), etc. The prediction engine 106 may update the 104 based on the attributes of the patient and the outcome data.

The process then uses (at step 510) the attributes and outcome data of the patients to train the machine learning model. In some embodiments, the prediction engine 106 may use a generic machine learning model (e.g., the lens compatibility model 212) to determine and/or predict a compatibility between patients and the type of lens (e.g., the same machine learning model is used to perform the prediction for every ECP). Thus, the model configuration module 208 may train the generic model (e.g., the lens compatibility model 212) based on the obtained attributes and outcome data. However, as discussed herein, different ECPs may emphasize certain attributes of a patient and de-emphasize other attributes of patients when recommending and/or prescribing the type of lens to the patients. The prediction engine 106 of some embodiments may enable an ECP to select, from a set of attributes, a subset of the attributes for determining a compatibility of the type of lens for patients, such that the input interface 400 may be customized for the ECP to prompt and obtain information corresponding only to the selected subset of attributes. Thus, the model configuration module 208 of some embodiments may configure a customized machine learning model (e.g., where the lens compatibility model 212 is a customized model) for the ECP such that the lens compatibility model 212 customized for the ECP 170 is configured to take only the subset of attributes selected by the ECP 170 as input data for determining and/or predicting a compatibility between patients and the type of lens.

Furthermore, different embodiments of the prediction engine 106 may configure the lens compatibility model 212 differently to generate the compatibility score to represent different facets of compatibility for the patients. For example, in some embodiments, the compatibility score may represent a predicted comfort level of the patient when wearing the lens. In another embodiment, the compatibility score may represent a predicted vision quality of the patient. In yet another embodiment, the compatibility score may represent a predicted number of lenses fitted for the patient and/or a predicted number of follow-up visits required by the patient. In yet another embodiment, the compatibility score may represent any combinations of the factors described above. The process of training the lens compatibility model 212 will be further described in detail below by reference to FIG. 7.

The process 500 then determines (at step 515) performance information associated with the different ECPs. For example, the performance assessment module 206 may determine performance information associated with the ECPs based on the obtained attributes and outcome data associated with patients of the ECPs. In some embodiments, the performance information determined by the performance assessment module 206 may include a ratio or a percentage of patients who were prescribed with the type of lens. For example, the performance assessment module 206 may determine a number of patients that were prescribed the type of lens by the ECP among the total number of patients associated with the ECP seeking the vision correction associated with the type of lens. The performance assessment module 206 may also determine multiple ratios or percentages, each corresponding to a particular recommendation (e.g., a particular compatibility index). Thus, the performance assessment module 206 may determine, for each compatibility index (e.g., a compatibility index corresponding to highly recommended, a compatibility index corresponding to recommended, a compatibility index corresponding to not recommended, etc.) a ratio or percentage of patients (for whom the compatibility index was determined) who were prescribed with the type of lens.

The performance information may also include, for those patients who were prescribed with the type of lens, the outcome data including the number of lenses fitted for the patient, the number of follow-up visits, the comfort quality, the vision quality, etc. The process then compares (at step 520) the performance information of a particular ECP against the performance information of the other ECPs and generates (at step 525) a performance metric for the particular ECP based on the comparison. For example, the performance assessment module 206 may compare the performance information of the ECP 170 against the performance information of other ECPs and generate a performance metric for the ECP 170. In some embodiments, the performance assessment module 206 may rank the ECPs based on one or more criteria, and the performance metric may include a ranking of the ECP 170 with respect to the other ECPs. The performance assessment module 206 may rank the ECPs for different criteria as well. Thus, the performance assessment module 206 may generate a first rankings for the ECPs based on the ratio of patients who were prescribed with the type of lens, may generate a second rankings for the ECPs based on the comfort level of the patients, may generate a third rankings for the ECPs based on the vision quality of the patients, may generate a fourth rankings for the ECPs based on the number of lenses fitted for the patient and/or the number of follow-up visits, and so forth. In some embodiments, the performance information may also indicate how the performance of the ECP (e.g., the ECP 170) changes (e.g., improve) over time. For example, the performance information may indicate that the comfort quality and/or the vision quality of the patients of the ECP 170 has improved over a period of time. The performance information may also indicate that the number of lenses fitted for the patient and/or the number of follow-up visits required by the patients of the ECP 170 has reduced over the period of time.

Referring back to FIG. 3, the process determines (at step 325) a compatibility between the patient and the type of lens by using a machine learning model. For example, the prediction manager 202 may use the lens compatibility model 212 (being trained at step 510 of FIG. 5) to determine a compatibility between the type of lens and the patient. For example, the lens compatibility model 212 may be configured to provide an output that indicates a likelihood that a patient is a good candidate for the type of lens (e.g., a compatibility score) based on attributes of the patient received via the user interface 400.

Figure 4B:
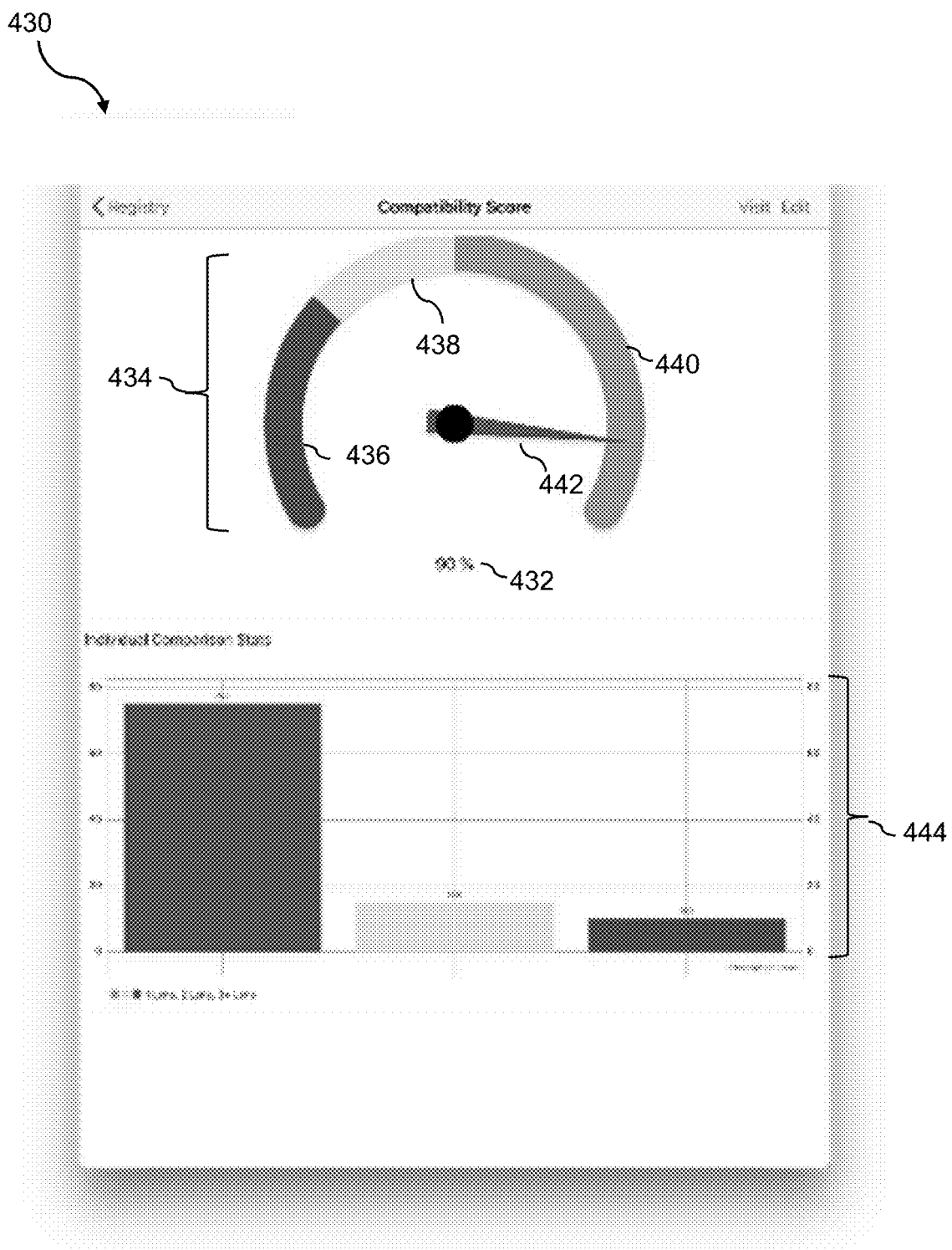
FIG. 4B illustrates an exemplary report interface according to some embodiments.

The process then generates (at step 330) a customized report indicating the determined compatibility for the ECP, where the report is customized based on the performance metric of the ECP. In some embodiments, the report generation module 204 of the prediction engine 106 may provide a compatibility report on an interface (e.g., a report interface) displayed on the ECP device 130 based on the output generated by the lens compatibility model 212. FIG. 4B illustrates an exemplary implementation of a report interface 430 generated by the report generation module 204. In this example, the report interface 430 includes the compatibility score 432 (e.g., 90%) determined by the lens compatibility model 212. As discussed herein, the compatibility score 432 indicates a likelihood that the patient is a good candidate for the type of lens. Since the lens compatibility model 212 was trained (at the step 510) using patient data of multiple ECPs (that may or may not include the ECP 170 who submitted the request), the ECP 170 who submitted the request may now obtain compatibility information for her patient based not only on how the type of lens fits patients of that ECP 170 in the past, but also how the type of lens would fit patients of other ECPs. The ability of the prediction engine 106 to access a large sample size of patients from different ECPs means that the accuracy of patient compatibility is improved. Furthermore, since the ECP 170 (who submitted the request) is only provided with the compatibility report generated by the prediction engine 106, and not any patient records used to train the lens compatibility model 212 (the ECP 170 does not have access to the patient records stored in the database 104, patient privacy may be preserved.

However, it may be difficult for the ECP 170 to translate the compatibility score to an actual recommendation for prescribing the type of lens to a patient. Thus, to assist the ECP 170 in her recommendation and/or prescription, the prediction manager 202 of some embodiments may derive additional data (e.g., meaning) to the compatibility score. For example, the prediction manager 202 may determine multiple compatibility indices that represent different recommendations for prescribing the type of lens to the patient. In a specific, but non-limiting example, the prediction manager 202 may determine three different compatibility indices, representing highly recommended, recommended, and not recommended, respectively. Different compatibility indices may be used for categorizing the compatibility scores in other embodiments. The compatibility indices may be associated with different, non-overlapping ranges of compatibility score. For example, if the compatibility score is generated on a scale of 1-100 by the lens compatibility model 212, a first range of 71-100 may correspond to a first compatibility index representing highly recommended, a second range of 41-70 may correspond to a second compatibility index representing recommended, and a third range of 1-40 may correspond to a third compatibility index representing not recommended. In some embodiments, the ranges may be determined based on specific outcomes of prescribing the type of lens to previous patients of the ECPs. In one example, the prediction manager 202 may determine the first range to include compatibility scores between 71-100 based on a predetermined percentage (e.g., 90% or any other predetermined percentage) of the patients prescribed with the type of lens having compatibility scores within this range never needed additional lens fitting and/or never needed a follow up visit with their ECPs. The prediction manager 202 may determine the second range to include compatibility scores between 41-70 based on a predetermined percentage (e.g., 90% or any other predetermined percentage) of the patients prescribed with the type of lens having compatibility scores within this range needed only one additional lens fitting and/or one follow up visit with their ECPs. The prediction engine 202 may then determine a compatibility index for the patient based on which of the ranges does the compatibility score fall into.

Thus, in some embodiments, the report generation module 204 may configure the report interface 430 to present, instead of or in addition to the compatibility score, the compatibility index on the interface to assist the ECP in recommending and/or prescribing the type of lens to the patient. In some embodiments, the prediction engine 106 may use the same compatibility score ranges for the compatibility indices for every ECPs. However, different ECPs may have different preferences in how they recommend or prescribe lenses to their patients. In certain scenarios, the differences in preferences may attribute to the demographics of the patients that the ECPs serve, the geographical area where the ECP is located, or ECPs' own personal preferences (e.g., how aggressive/conservative they are in prescribing the type of lens to patients). Since the lens compatibility model 212 was trained with historical data of patients of different ECPs, and the model 212 does not differentiate one ECP from another, the output (e.g., the compatibility score) of the lens compatibility model 212 may be generic to all patients, and not specific to patients of one ECP (e.g., the ECP 170). As such, in some embodiments, the prediction engine 106 may determine different ranges corresponding to the different compatibility indices for different ECPs. For example, the prediction manager 202 may determine, for the ECP 170, that the first compatibility index (e.g., highly recommended) corresponds to a range of 81-100, the second compatibility index (e.g., recommended) corresponds to a range of 51-80, and the third compatibility index (e.g., recommended) corresponds to a range of 1-50. The lens compatibility system may determine, for a second ECP, that the first compatibility index (e.g., highly recommended) corresponds to a range of 61-100, the second compatibility index (e.g., recommended) corresponds to a range of 31-60, and the third compatibility index (e.g., recommended) corresponds to a range of 1-30.

The different ranges may be determined for the different ECPs based on various factors, such as the geographical area of the ECPs, the demographics of the patients of the ECPs, or a recommendation/prescription performance of the ECP (e.g., the ECP 170) relative to the performance of other ECPs (e.g., the ECP's peers). As such, in some embodiments, the prediction manager 202 may determine a position of the ECP 170 who submitted the request in comparison with the positions of other ECPs based on the recommendation/prescription performances of the ECPs. For example, the prediction manager 202 may use the performance metrics (determined at the step 320) associated with the different ECPs (including the ECP 170) to determine the different ranges for the different compatibility indices. As discussed herein, the performance metric associated with the ECP 170 may include a ratio or a percentage of patients who were prescribed with the type of lens, a number of lenses fitted for the patient who sought the type of lens, a number of follow-up visits from patients who were prescribed with the type of lens, a comfort quality level of the patients who were prescribed with the type of lens, a vision quality level of the patients who were prescribed with the type of lens, and others as described herein. The Performance metric may also include a ranking of the ECP 170 with respect to the other ECPs based on these performance metrics. The prediction manager 202 may then determine the different ranges for the different compatibility indices based on the performance metrics and/or the ranking of the ECP 170. In a specific, and non-limiting, example, if the prediction manager 202 determines that the ECP 170 has a lower than average ratio compared to the other ECP (a lower ranking for that performance criterion), the prediction manager 202 may enlarge the range(s) corresponding to the first (and/or second) compatibility indices (representing highly recommended and recommended, respectively), and vice versa. In another example, if the prediction manager 202 determines that the ECP 170 has a lower number of lenses fitted for the patient and/or a lower number of follow-up visits compared to the other ECP (a lower ranking for that performance criterion), the lens compatibility system may enlarge the range(s) corresponding to the first (and/or second) compatibility indices (representing highly recommended and recommended, respectively), and vice versa.

As shown in FIG. 4B, the report interface 430 includes a graphical representation 434 of the compatibility index determined for the patient of the ECP 170. In this example, the graphical representation 434 is implemented in the form of a gauge that is divided into three sections 436, 438, and 440. Each of the sections 436-440 corresponds to a distinct compatibility index determined by the prediction engine 106. For example, the section 436 corresponds to the third compatibility index representing a 'not recommended' recommendation, the section 438 corresponds to the second compatibility index representing a 'recommended' recommendation, and the section 440 corresponds to the first compatibility index representing a 'highly recommended' recommendation. Since the compatibility score of 90% falls within the score range (81-100) corresponds to the first compatibility index, the graphical representation 434 includes an indicator 442 pointing to the section 440 of the gauge that corresponds to the 'highly recommended' recommendation.

In addition to the compatibility score and the compatibility index, the report generation module 204 of some embodiments may configure the report interface 430 to include other analytical information that may assist the ECP 170 to provide the recommendation and/or prescription for the patient. The analytical information may be determined based on the compatibility scores and/or compatibility indices determined for previous patients of different ECPs (that may or may not include the ECP 170). For example, the prediction manager 202 may determine a number of patients that have been assigned with the first compatibility index, a number of patients that have been assigned with the second compatibility index, and a number of patients that have been assigned with the third compatibility index. As shown in FIG. 4B, the report interface 430 may be configured by the report generation module 204 to include a representation (e.g., a graph 444) indicating the distribution of patients in the three compatibility indices.

After the compatibility report is presented to the ECP 170 via the report interface 430, the ECP 170 may decide whether to recommend and/or prescribe the type of lens to the patient based on the compatibility report. In some embodiments, after providing the compatibility report to the ECP 170, the prediction manager 202 may generate and provide a feedback interface to the ECP 170 to obtain outcome feedback regarding the patient. For example, through the feedback interface, the ECP 170 may indicate to the prediction engine 106 whether the ECP 170 has recommended and/or prescribed the type of lens to the patient. Furthermore, if the ECP 170 indicates that she has recommended and/or prescribed the type of lens to the patient, the ECP 170 may also provide feedback information representing an outcome of the prescription. For example, the ECP 170 may indicate the number of lenses actually fitted for the patient and/or the number of follow-up visits actually conducted by the patient following the recommendation and/or the prescription of the type of lens. The ECP 170 may also indicate the comfort level and vision quality of the patient (e.g., through an evaluation and/or a survey) when using the type of lens.

Figure 4C:
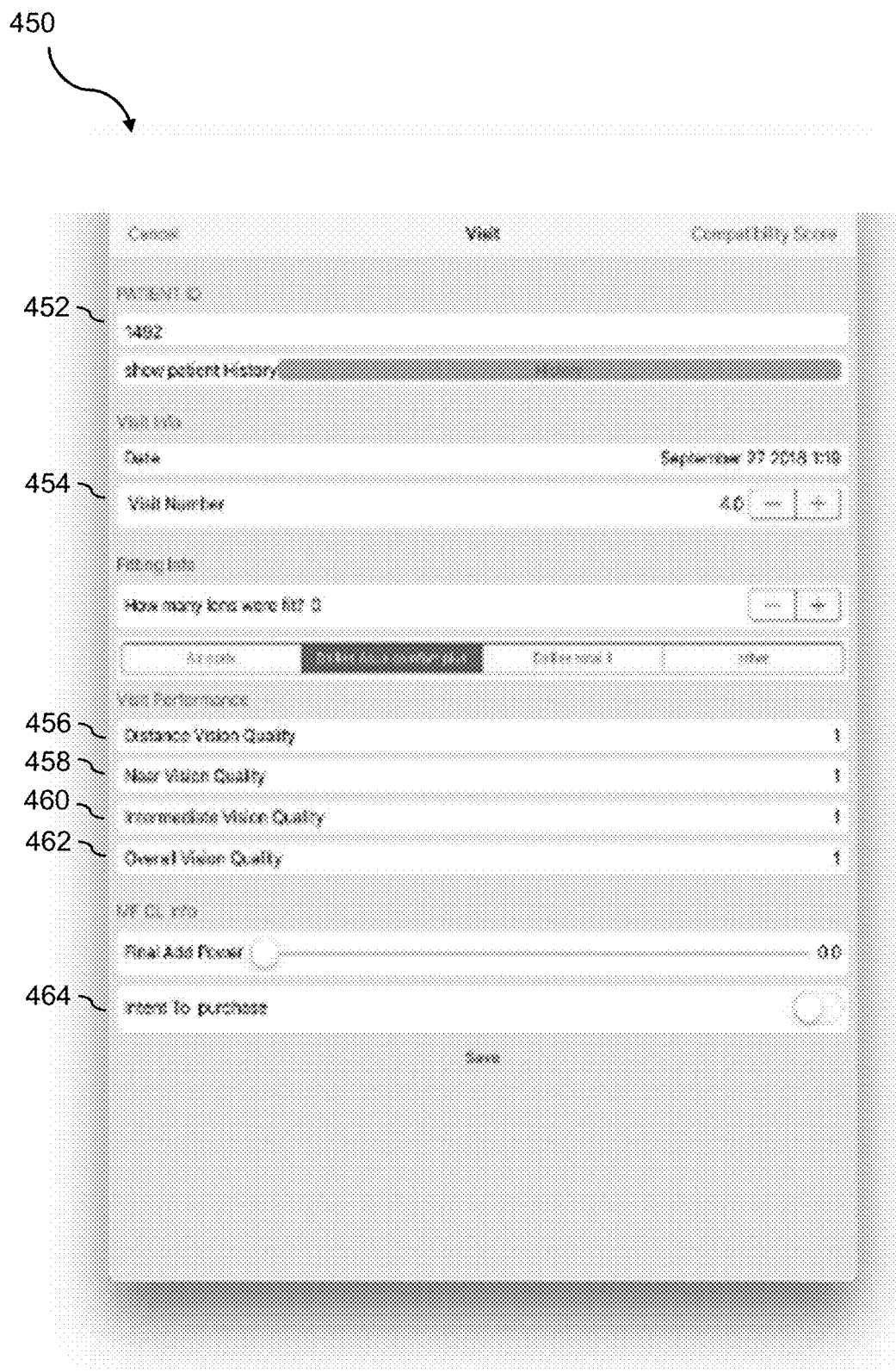
FIG. 4C illustrates an exemplary feedback interface according to some embodiments.

FIG. 4C illustrates an exemplary implementation of a feedback interface 450 according to an embodiment of the disclosure. As shown, the feedback interface 450 includes an input field 452 that indicates an identity of the patient. The identity of the patient can be generated for the patient when the compatibility request was submitted to the prediction engine 106 via the input interface 400. In this example, the input field 452 includes the patient identifier '1492.' The feedback interface 450 also includes a field 454 corresponding to the number of lenses fitted for the patient and/or the number of follow-up visits by the patient. The feedback interface 450 also includes fields 456-462 representing the vision qualities, including the distance vision quality 456, the near vision quality 458, the intermediate vision quality 460, and overall vision quality 462. Furthermore, the feedback interface 450 also includes a field 464 representing whether the patient intends to purchase the type of lens. Thus, the ECP 170 may provide the information corresponding to the fields 454-464 regarding the outcome of recommending and/or prescribing the type of lens to the patient. Upon receiving the feedback information from the ECP device 130 via the feedback interface 450, the prediction engine 106 may update the database 106 based on the attributes of the patient (obtained via the input interface 400 and the vision simulator 160) and the feedback information (obtained via the feedback interface 450). For example, the prediction engine 106 may generate a new patient record based on the attributes of the patient and the feedback information, and may add the new patient record to the database 104. In some embodiments, the model configuration module 208 may use the updated database 104 to train (or re-train) the lens compatibility model 212 such that the lens compatibility model 212 can be continuously modified and/or updated based on new cases (e.g., new patient records). In some embodiments, the performance assessment module 206 may also use the updated database 104 to determine an updated performance metric for ECP 170 and/or other ECPs.

Figure 4D:
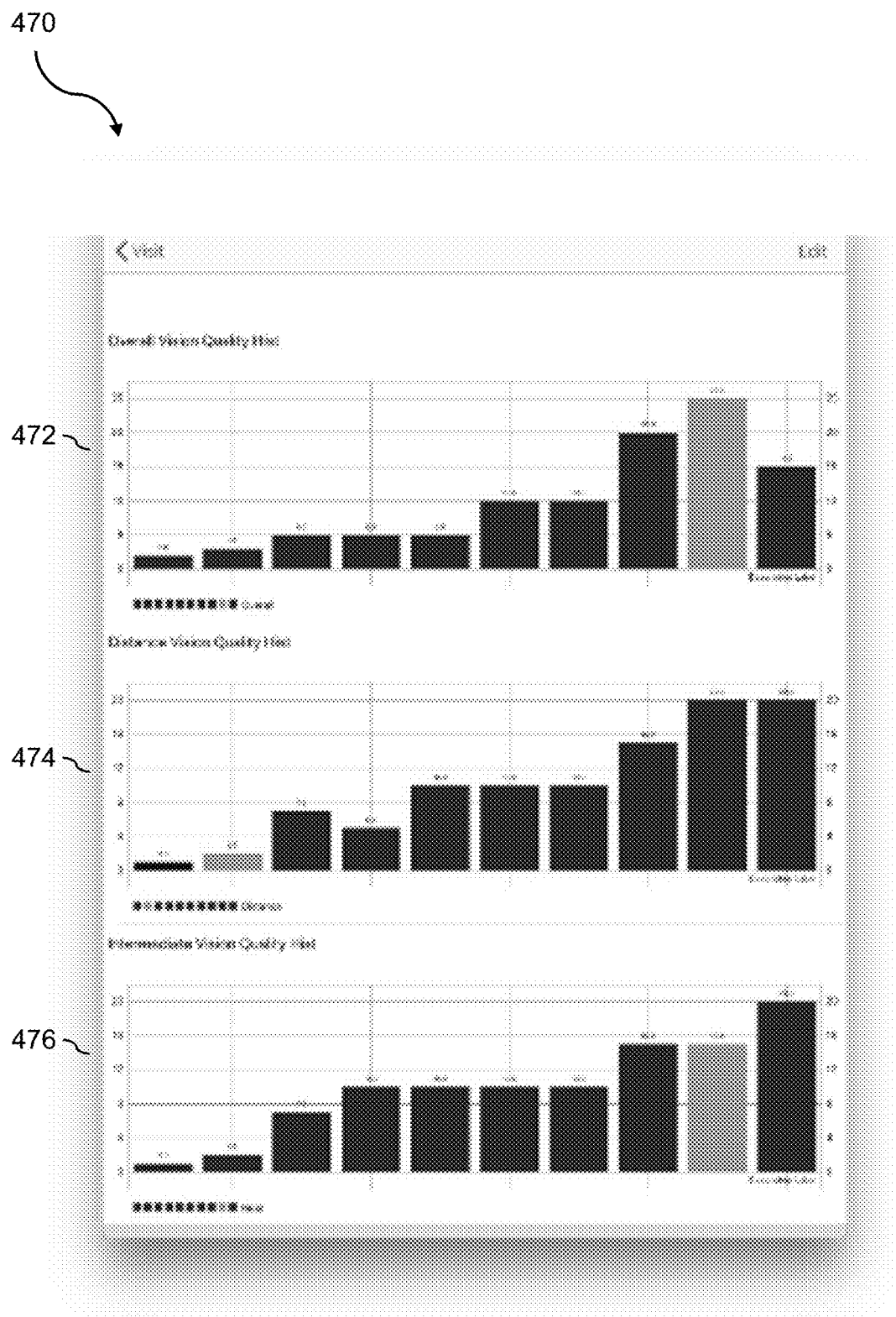
FIG. 4D illustrates an exemplary performance interface according to some embodiments.

Furthermore, the prediction manager 202 may provide to the ECP 170 performance information regarding the patient with respect to other patients who have been prescribed the type of lens. FIG. 4D illustrates a performance interface 470 representing the performance of the patient of the ECP 170 with respect to other patients who have been prescribed with the type of lens. For example, the performance interface 470 includes a histogram 472 representing where the patient's overall vision quality stands among other patients, a histogram 474 representing where the patient's distance vision quality stands among other patients, and a histogram 476 representing where the patient's intermediate vision quality stands among other patients. Other graphs or representation representing these performance criteria (or other performance criteria) may also be included in the performance interface 470.

Figure 4E:
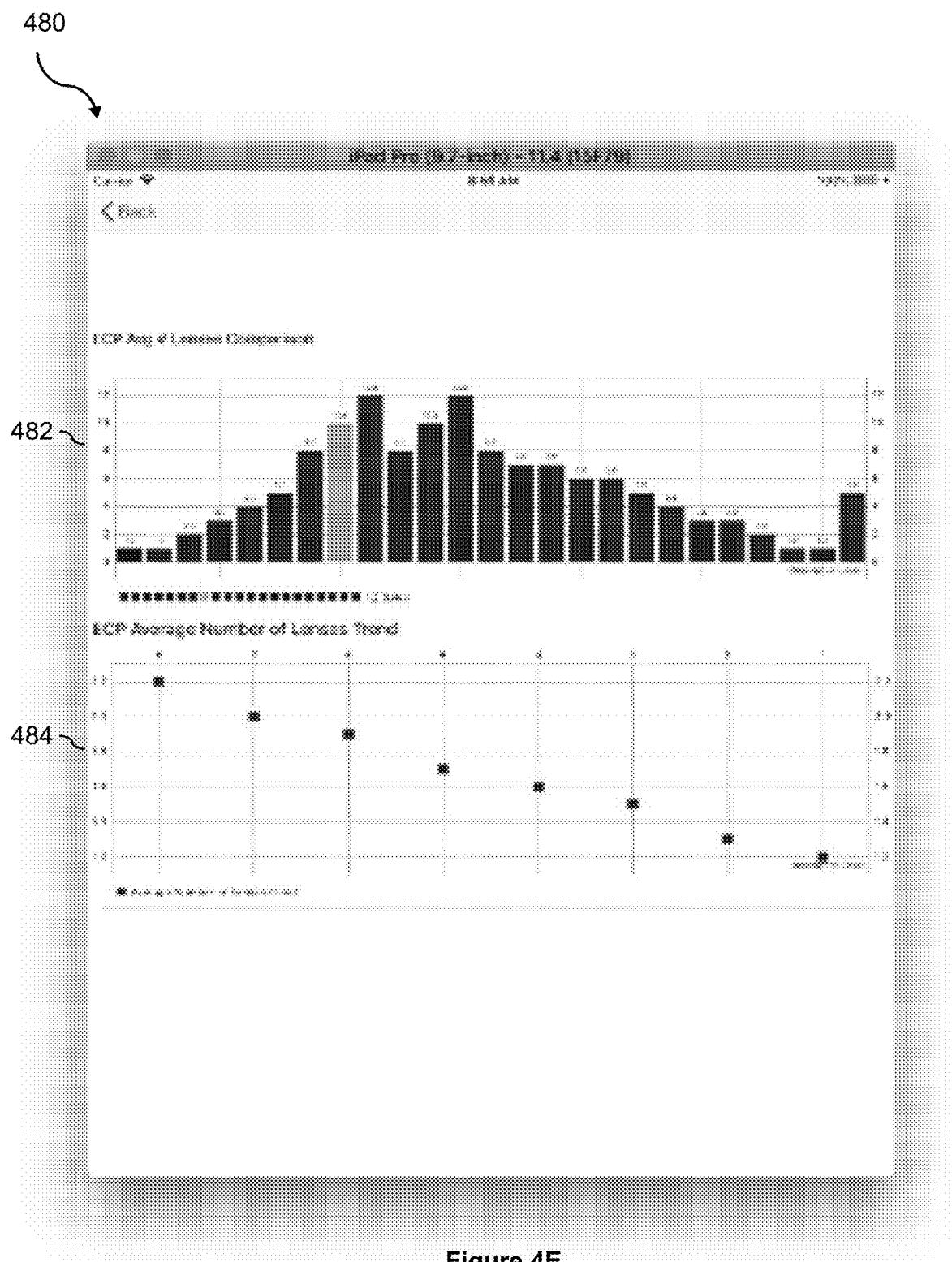
FIG. 4E illustrates another exemplary performance interface according to some embodiments.

FIG. 4E illustrates an exemplary implementation of another performance interface 480 presenting performance information regarding the ECP 170 with respect to other ECPs that may be provided by the prediction manager 202. As shown in the figure, the performance interface 480 includes a performance histogram 482 representing where the ECP 170 stands in terms of the ratio of patients being prescribed with the type of lens with respect to other ECPs. The performance interface 480 also includes a graph 484 representing a trend of a number of the type of lens being prescribed by the ECP 170 over a period of time.

While the description above describes the process of determining compatibility using the example of contact lenses, and more specifically, multi-focal contact lenses, it has been envisioned that the process of determining customized compatibility for ECPs described herein can be used to determine compatibility of other lenses, such as other types of contact lenses, etc.

Figure 6A:
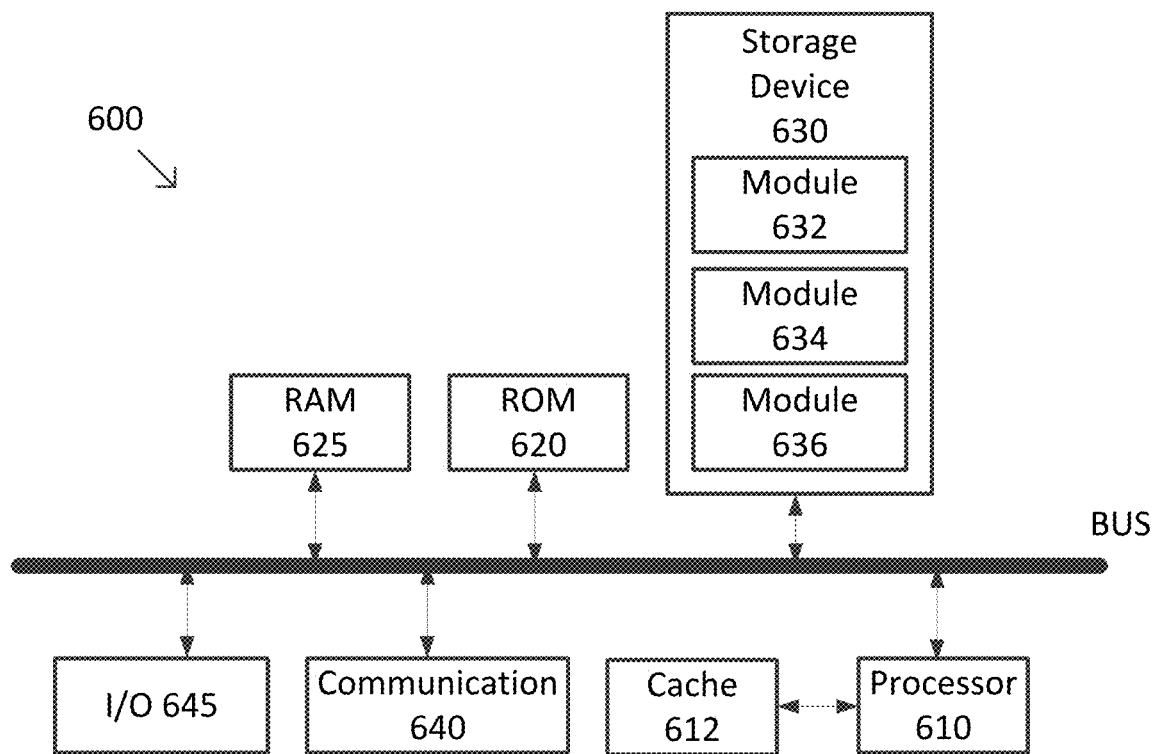
FIGS. 6A and 6B are diagrams of processing systems according to some embodiments.
Figure 6B:
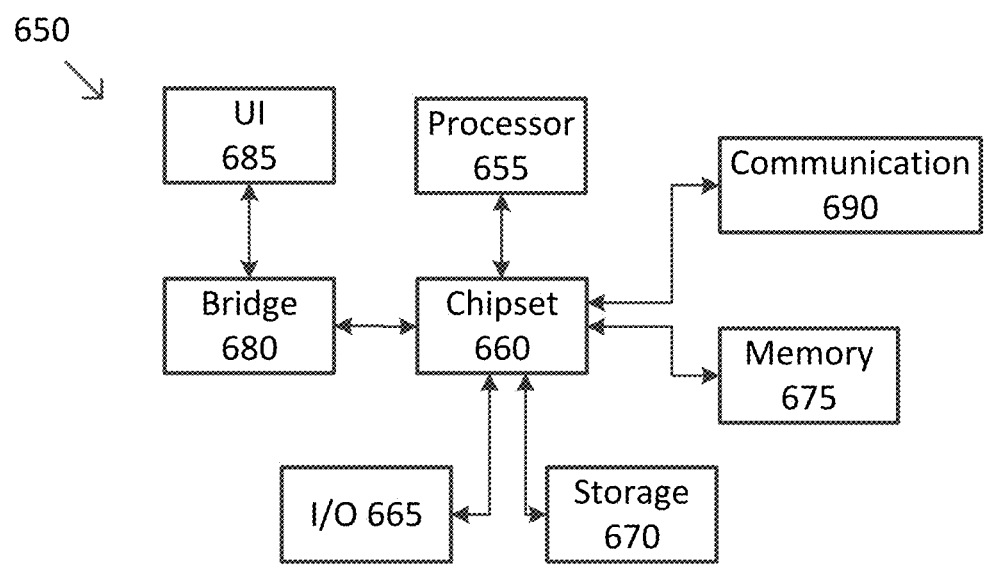

FIGS. 6A and 6B are diagrams of processing systems according to some embodiments. Although two embodiments are shown in FIGS. 6A and 46B, persons of ordinary skill in the art will also readily appreciate that other system embodiments are possible. According to some embodiments, the processing systems of FIGS. 6A and/or 6B are representative of computing systems that may be included in one or more of lens selection platform 102, the ECP devices 130, 140, and 150, the diagnostic training data source(s) 110, the vision simulator 160, and/or the like.

FIG. 6A illustrates a computing system 600 where the components of system 600 are in electrical communication with each other using a bus 605. System 600 includes a processor 610 and a system bus 605 that couples various system components including memory in the form of a read only memory (ROM) 620, a random access memory (RAM) 625, and/or the like (e.g., PROM, EPROM, FLASH-EPROM, and/or any other memory chip or cartridge) to processor 610. System 600 may further include a cache 612 of high-speed memory connected directly with, in close proximity to, or integrated as part of processor 610. System 600 may access data stored in ROM 620, RAM 625, and/or one or more storage devices 630 through cache 612 for high-speed access by processor 610. In some examples, cache 612 may provide a performance boost that avoids delays by processor 610 in accessing data from memory 615, ROM 620, RAM 625, and/or the one or more storage devices 630 previously stored in cache 612. In some examples, the one or more storage devices 630 store one or more software modules (e.g., software modules 632, 634, 636, and/or the like). Software modules 462, 634, and/or 636 may control and/or be configured to control processor 610 to perform various actions, such as the processes of methods 300 and/or 500. And although system 600 is shown with only one processor 610, it is understood that processor 610 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, system 400 may be implemented as a stand-alone subsystem and/or as a board added to a computing device or as a virtual machine.

To enable user interaction with system 600, system 600 includes one or more communication interfaces 640 and/or one or more input/output (I/O) devices 645. In some examples, the one or more communication interfaces 640 may include one or more network interfaces, network interface cards, and/or the like to provide communication according to one or more network and/or communication bus standards. In some examples, the one or more communication interfaces 440 may include interfaces for communicating with system 600 via a network, such as network 115. In some examples, the one or more I/O devices 645 may include on or more user interface devices (e.g., keyboards, pointing/selection devices (e.g., mice, touch pads, scroll wheels, track balls, touch screens, and/or the like), audio devices (e.g., microphones and/or speakers), sensors, actuators, display devices, and/or the like).

Each of the one or more storage devices 630 may include non-transitory and non-volatile storage such as that provided by a hard disk, an optical medium, a solid-state drive, and/or the like. In some examples, each of the one or more storage devices 630 may be co-located with system 600 (e.g., a local storage device) and/or remote from system 600 (e.g., a cloud storage device).

FIG. 6B illustrates a computing system 650 based on a chipset architecture that may be used in performing any of the methods (e.g., methods 300 and/or 510) described herein. System 650 may include a processor 655, representative of any number of physically and/or logically distinct resources capable of executing software, firmware, and/or other computations, such as one or more CPUs, multi-core processors, microprocessors, microcontrollers, DSPs, FPGAs, ASICs, GPUs, TPUs, and/or the like. As shown, processor 655 is aided by one or more chipsets 660, which may also include one or more CPUs, multi-core processors, microprocessors, microcontrollers, DSPs, FPGAs, ASICs, GPUs, TPUs, co-processors, coder-decoders (CODECs), and/or the like. As shown, the one or more chipsets 660 interface processor 655 with one or more of one or more I/O devices 665, one or more storage devices 670, memory 675, a bridge 680, and/or one or more communication interfaces 690. In some examples, the one or more I/O devices 665, one or more storage devices 670, memory, and/or one or more communication interfaces 690 may correspond to the similarly named counterparts in FIG. 6A and system 600.

In some examples, bridge 680 may provide an additional interface for providing system 650 with access to one or more user interface (UI) components, such as one or more keyboards, pointing/selection devices (e.g., mice, touch pads, scroll wheels, track balls, touch screens, and/or the like), audio devices (e.g., microphones and/or speakers), display devices, and/or the like. According to some embodiments, systems 600 and/or 650 may provide a graphical user interface (GUI) suitable for aiding a user (e.g., a surgeon and/or other medical personnel) in the performance of the processes of methods 300 and/or 500.

Figure 7:
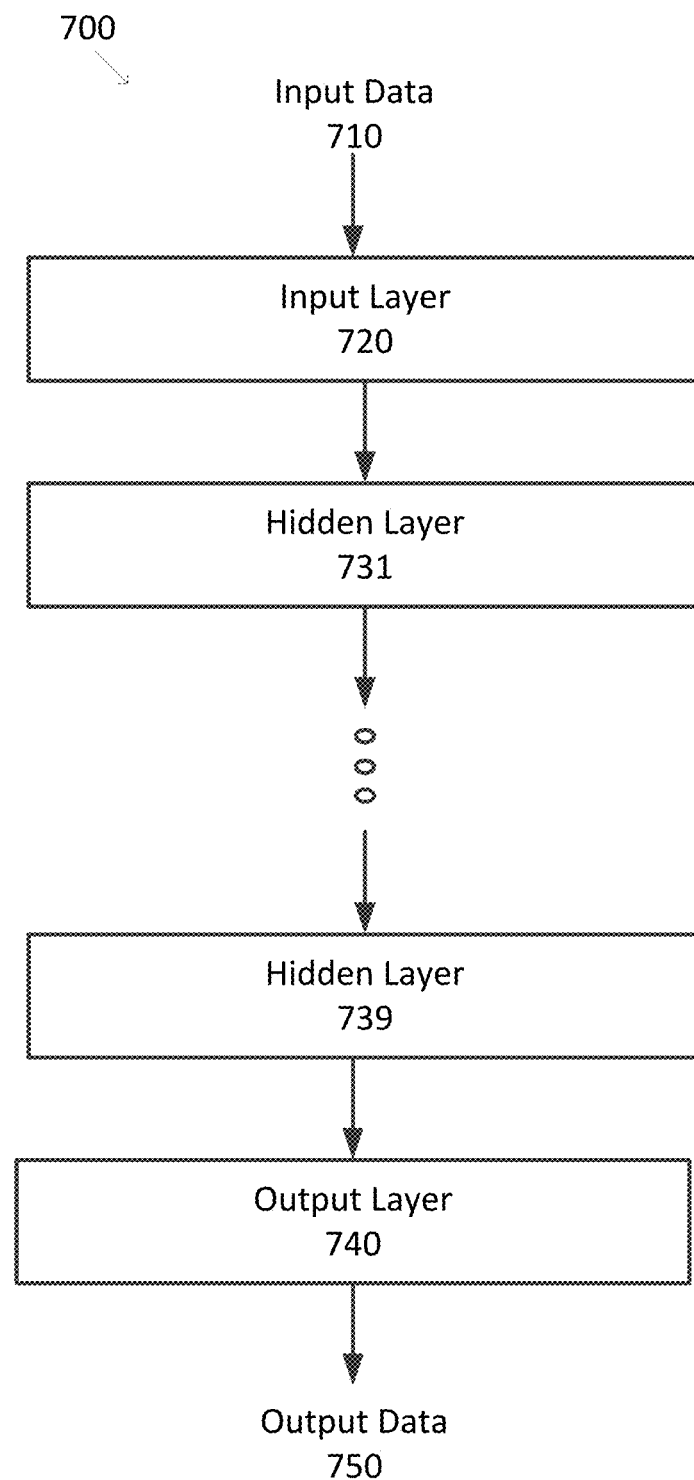
FIG. 7 is a diagram of a multi-layer neural network according to some embodiments.

FIG. 7 is a diagram of a multi-layer neural network 700 according to some embodiments. In some embodiments, neural network 700 may be representative of a neural network used to implement at least some of the machine learning models (including the lens compatibility model 212) used by prediction engine 106. While a neural network 700 is illustrated herein for implementing the machine learning models in this example, one or more of the machine learning models may be implemented using other machine learning techniques such as regression models, etc. Neural network 700 processes input data 710 using an input layer 720. In some examples, input data 710 may correspond to the input data provided to the one or more models and/or the training data provided to the one or more models during the training process (e.g., step 510 of the process 500) used to train the one or more models. Input layer 720 includes a plurality of neurons that are used to condition input data 710 by scaling, range limiting, and/or the like. Each of the neurons in input layer 720 generates an output that is fed to the inputs of a hidden layer 731. Hidden layer 731 includes a plurality of neurons that process the outputs from input layer 720. In some examples, each of the neurons in hidden layer 731 generates an output that are then propagated through one or more additional hidden layers that end with hidden layer 739. Hidden layer 739 includes a plurality of neurons that process the outputs from the previous hidden layer. The outputs of hidden layer 739 are fed to an output layer 740. Output layer 740 includes one or more neurons that are used to condition the output from hidden layer 739 by scaling, range limiting, and/or the like. It should be understood that the architecture of neural network 700 is representative only and that other architectures are possible, including a neural network with only one hidden layer, a neural network without an input layer and/or output layer, a neural network with recurrent layers, and/or the like.

In some examples, each of input layer 720, hidden layers 731-739, and/or output layer 740 includes one or more neurons. In some examples, each of input layer 720, hidden layers 731-739, and/or output layer 740 may include a same number or a different number of neurons. In some examples, each of the neurons takes a combination (e.g., a weighted sum using a trainable weighting matrix W) of its inputs x, adds an optional trainable bias b, and applies an activation function f to generate an output a as shown in Equation 1 below. In some examples, the activation function f may be a linear activation function, an activation function with upper and/or lower limits, a log-sigmoid function, a hyperbolic tangent function, a rectified linear unit function, and/or the like. In some examples, each of the neurons may have a same or a different activation function.

$$a = f(Wx+b) \hspace{2cm} \text{Equation (1)}$$

In some examples, neural network 700 may be trained using supervised learning where combinations of training data that include a combination of input data and a ground truth (e.g., expected) output data. Differences between the output of neural network 700 as generated using the input data for input data 710 and comparing output data 750 as generated by neural network 700 to the ground truth output data. Differences between the generated output data 750 and the ground truth output data may then be fed back into neural network 700 to make corrections to the various trainable weights and biases. In some examples, the differences may be fed back using a back propagation technique using a stochastic gradient descent algorithm, and/or the like. In some examples, a large set of training data combinations may be presented to neural network 700 multiple times until an overall loss function (e.g., a mean-squared error based on the differences of each training combination) converges to an acceptable level.

Methods according to the above-described embodiments may be implemented as executable instructions that are stored on non-transitory, tangible, machine-readable media. The executable instructions, when run by one or more processors (e.g., processor 610 and/or processor 655) may cause the one or more processors to perform one or more of the processes of methods 200 and/or 210. Some common forms of machine-readable media that may include the processes of methods 200 and/or 210 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Devices implementing methods according to these disclosures may comprise hardware, firmware, and/or software, and may take any of a variety of form factors. Typical examples of such form factors include laptops, smart phones, small form factor personal computers, personal digital assistants, and/or the like. Portions of the functionality described herein also may be embodied in peripherals and/or add-in cards. Such functionality may also be implemented on a circuit board among different chips or different processes executing in a single device, by way of further example.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system, comprising:
    a non-transitory memory; and
    one or more hardware processors coupled with the non-transitory memory and configured to read instructions from the non-transitory memory to cause the system to perform operations comprising:
        receiving, from a first device associated with a first eye-care professional (ECP), a request for selecting a contact lens for a consumer, wherein the request comprises biometric information associated with the consumer;
        obtaining a performance metric associated with the first ECP;
        determining, using the machine learning model and based on the performance metric, a customized compatibility index indicating a compatibility between a particular contact lens and the consumer for the first ECP;
        generating, using the machine learning model, a compatibility score based on the biometric information;
        identifying, from a plurality of compatibility indexes, the customized compatibility index for the first ECP based on the compatibility score and the performance metric associated with the first ECP; and
        presenting a report indicating the customized compatibility index on the first device.

2. The system of claim 1, wherein the performance metric represents relative compatibilities between contact lenses and first consumers associated with the first ECP with respect to compatibilities between contact lenses and second consumers associated with at least a second ECP.

3. The system of claim 1, wherein the plurality of compatibility indexes corresponds to distinct compatibility score ranges, wherein the determining the compatibility index further comprises:
    adjusting the distinct compatibility score ranges based on the performance metric to generate customized compatibility score ranges for the first ECP, wherein the identifying is further based on the customized compatibility score ranges corresponding to the plurality of compatibility indexes.

4. The system of claim 1, wherein the compatibility score represents at last a predicted vision quality of the consumer using the contact lens.

5. The system of claim 4, wherein the predicted vision quality comprises a predicted distance vision quality, a predicted near vision quality, and a predicted intermediate vision quality.

6. The system of claim 1, wherein the biometric information comprises an arm length of the consumer.

7. The system of claim 1, wherein the report includes statistics of vision qualities of consumers using the contact lens.

8. A non-transitory machine-readable medium having stored thereon machine-readable instructions executable to cause a machine to perform operations comprising:
    receiving, from a first device associated with a first eye-care professional (ECP), a request for selecting a contact lens for a consumer, wherein the request comprises biometric information associated with the consumer;
    obtaining a performance metric associated with the first ECP;
    determining, using the machine learning model and based on the performance metric, a customized compatibility index indicating a compatibility between a particular contact lens and the consumer for the first ECP;
    generating, using the machine learning model, a compatibility score based on the biometric information;
    identifying, from a plurality of compatibility indexes, the customized compatibility index for the first ECP based on the compatibility score and the performance metric associated with the first ECP; and
    presenting a report indicating the customized compatibility index on the first device.

9. The non-transitory machine-readable medium of claim 8, wherein the operations further comprise:
    obtaining vision quality data of the patient using the particular contact lens; and
    using the biometric information and the vision quality data to further train the machine learning model.

10. The non-transitory machine-readable medium of claim 8, wherein the operations further comprise:
    obtaining biometric data and vision quality data associated with a plurality of consumers from at least a second device associated with a second ECP; and
    training the machine learning model using the obtained biometric data and the vision quality data.

11. The non-transitory machine-readable medium of claim 8, wherein the performance metric represents a comparison between compatibilities between contact lenses and first consumers associated with the first ECP and compatibilities between contact lenses and second consumers associated with at least a second ECP.

12. The non-transitory machine-readable medium of claim 8, wherein the plurality of compatibility indexes corresponds to distinct compatibility score ranges, wherein the determining the compatibility index further comprises:
    adjusting the distinct compatibility score ranges based on the performance metric to generate customized compatibility score ranges for the first ECP, wherein the identifying is further based on the customized compatibility score ranges corresponding to the plurality of compatibility indexes.

13. The non-transitory machine-readable medium of claim 8, wherein the compatibility score represents a predicted comfort level of the consumer using the contact lens.

* * * * *